United States Patent [19]
Hobby

[11] Patent Number: 5,279,963
[45] Date of Patent: Jan. 18, 1994

[54] SYSTEM FOR THE DECONTAMINATION OF A CONTAMINATED GAS

[76] Inventor: Michael M. Hobby, 2700 Sunset Rd., Ste. D31, Las Vegas, Nev. 89120

[21] Appl. No.: 687,395

[22] Filed: Apr. 18, 1991

[51] Int. Cl.[5] .............................................. A61L 9/01
[52] U.S. Cl. ........................................ 435/266; 5/228; 210/631; 435/31; 435/299; 435/311; 435/313; 435/315; 95/187; 95/234
[58] Field of Search .................... 55/89, 90, 228; 435/266, 31, 299, 311, 313, 315; 210/601, 605, 611, 617, 622, 625, 631, 195.1, 199, 202, 721, 760, 912

[56] References Cited

U.S. PATENT DOCUMENTS

| | | | |
|---|---|---|---|
| 3,719,028 | 3/1973 | Brooks | 55/85 |
| 4,427,548 | 1/1984 | Quick, Jr. | 210/617 |
| 4,472,181 | 9/1984 | Herrlander | 55/228 |
| 4,710,301 | 12/1987 | Geuens | 210/605 |
| 4,738,695 | 4/1988 | Carr et al. | 55/84 |
| 4,781,732 | 11/1988 | Wondrasch et al. | 55/10 |
| 4,849,114 | 7/1989 | Zeff et al. | 210/747 |
| 4,940,546 | 7/1990 | Vogelpohl et al. | 210/613 |
| 4,970,000 | 11/1990 | Eppler et al. | 210/605 |
| 4,999,302 | 3/1991 | Kahler et al. | 435/266 |
| 5,017,351 | 5/1991 | Rafson | 423/245.2 |
| 5,039,416 | 8/1991 | Loew et al. | 210/631 |
| 5,077,025 | 12/1991 | Glass | 423/245.1 |
| 5,077,208 | 12/1991 | Sublette | 435/168 |

FOREIGN PATENT DOCUMENTS 3601490 7/1987 Fed. Rep. of Germany .

Primary Examiner—Robert J. Warden
Assistant Examiner—Krisanne M. Thornton
Attorney, Agent, or Firm—Jon C. Christiansen

[57] ABSTRACT

A decontamination system and method for the decontamination of a contaminated gas. The contaminated gas is characterized by a gas phase and at least one contaminant. The contaminated gas is removed from its source and is introduced into a loop through which a bio-agent is circulated. The bio-agent includes a microorganism (e.g. bacterium) effective for the biodegradation of the contaminant. The bio-agent may also include a liquid carrier. The loop may include absorption column, separator and bioreactor positioned in the loop. An oxidation means can be utilized to oxidize metals in the contaminated gas. Alternatively, the bio-agent can be replaced by a liquid which circulates through the bioreactor and which is effective for absorption of the contaminant. In other embodiments, the loop can be replaced by a conduit in a form or arrangement other than a loop.

98 Claims, 2 Drawing Sheets

SYSTEM FOR THE DECONTAMINATION OF A CONTAMINATED GAS

INTRODUCTION

My invention relates to systems (including apparatus) and methods for the decontamination of contaminated gases (including vapors). My invention provides solutions to a variety of environmental problems created by the widespread existence of contaminated gases in various forms and from various sources. Increasingly, environmental concerns, as well as environmental laws and regulations, are necessitating the implementation of more effective control and clean-up of contaminated gases. Present technologies are either ineffective (or partially ineffective) or require substantial capital and operating expenditures. One objective of my invention is to provide a more effective decontamination technology that can be implemented and operated at a cost lower than alternative decontamination technologies.

My invention can be used in connection with the degassing of tanks. As used herein, "tanks" shall mean tanks and other storage vessels in which an enclosed atmosphere is contained. The enclosed atmosphere includes a contaminated gas. For example, a tank containing gasoline, petroleum, or other hydrocarbons may include an enclosed atmosphere in which volatile organic compounds (e.g. benzene, toluene, xylene, etc.) may reside in the gas phase. The enclosed atmosphere in a tank may alternatively or additionally include other contaminants such as sulfur oxides ($SO_x$) and nitrogen oxides ($NO_x$). Although the tanks could be degassed by simply venting the contaminated gas from the enclosed atmosphere into the earth's atmosphere, such venting would be environmentally unsound and, in some cases, may be in violation of environmental laws or regulations. Accordingly, it is necessary to deal with the contaminants rather than to release them into the earth's atmosphere. Activated carbon and internal combustion engines are typically utilized to destroy volatile organic compounds in the contaminated gas. The use of activated carbon for this purpose results in contaminated carbon which must be treated or disposed of. The use of an internal combustion engine results in combustion by-products which are discharged to the earth's atmosphere or treated with a catalytic converter to remove contamination. One purpose of my invention is to provide for a more economical and more effective means of decontamination of such contaminated gases and which can provide for the destruction of contaminants via biodegradation.

My invention can also be used in connection with the treatment of contaminated gas streams from industrial processes and facilities. For example, a stack from a steel mill spews a contaminated air stream into earth's atmosphere. Such contaminated air stream may contain contaminants such as organic compounds (e.g. benzene, toluene, isoprene, etc.) as well as sulfur oxides and nitrogen oxides. Scrubbers and other devices or processes are typically used to reduce the resultant pollution but are not without disadvantages and/or substantial expense. Scrubbers, for example, can remove some contamination from the air stream (or other gas stream) but require substantial capital expenditures and produce contaminated liquid streams which must be treated or disposed of. My invention can be used to provide a more economical and more effective means of decontamination of contaminated gases from industrial processes and facilities (e.g. steel mills, refineries, chemical facilities, etc.). My invention provides for the destruction of contaminants in such gas stream via biodegradation.

My invention can also be used in connection with the treatment of contaminated vapors extracted from contaminated soils. For example, volatile organic compounds trapped in the vadose zone between the surface and the groundwater, which may originate from spills or tank leaks, or from free product floating on the groundwater. Such contaminated vapors are typically extracted from contaminated soil by vacuum pumps or blowers or other means of vapor extraction. The contaminants in such extracted vapor can be, for example, gasoline components, solvents, or chemicals from line leaks in the ground (subsurface). My invention provides for the destruction of such contaminants via biodegradation within a loop, preferably a closed loop which isolates the atmosphere from the contamination.

My invention can also be used in connection with the treatment of a contaminated gas stream from a stripper (e.g. a stripping column). The stripper is a means for stripping volatile contaminants from a liquid into a gas. Contaminated gas exits the stripper and may now or eventually require treatment to prevent environmental pollution. My invention can be employed to treat contaminants in such gas by destroying the contaminants via biodegradation.

More broadly, my invention has application to any gas containing contaminants which are susceptible to biodegradation as more fully explained below.

SUMMARY OF THE INVENTION

My invention is a decontamination system for the decontamination of contaminated gas includes a gas phase and at least one contaminant. Contaminated gas is removed from its source and introduced into a loop. A bio-agent is circulated through the loop. The bio-agent includes a microorganism (e.g. a bacterium) effective for the biodegration of the contaminant. Preferably, the bio-agent also includes a liquid carrier (e.g. water or a water-based solution).

Biodegradation (i.e. digestion) in the loop or conduit (or in a bioreactor as described below) can be accomplished through the use of aerobic bacteria (or anaerobic bacteria) which are effective for the biodegradation of the contaminants in question. Aerobic bacteria (which are active in the presence of oxygen) convert organic materials into carbon dioxide, water and biomass (more bacteria). There may also remain some undigested solids. Anaerobic bacteria digest organic materials in the absence of oxygen and may be suitable for biodegradation of some contaminants. The by-products of digestion by anaerobic bacteria include water and gases, such as methane and hydrogen sulfide. (Note: these gases may be subject to biodegradation by aerobic bacteria within a second loop).

The contaminated gas is introduced into the loop for contact with the circulating bio-agent. The microorganism (e.g. bacterium) biodegrades the contaminant. The liquid carrier can absorb contaminant from the gas phase to facilitate biodegradation of the contaminant by the microorganism. The loop can include an absorption column, a separator and a bioreactor positioned in the loop.

The absorption column facilitates absorption of the contaminant and can also serve as a pre-separation bioreactor. The separator separates the gas phase from the bio-agent (and absorbed contaminant) for removal from the loop. The bioreactor provides further opportunity for biodegradation of the contaminant. The bio-agent (and absorbed contaminant) and biodegradation products are circulated through the loop back to the absorption column. More than one absorption column, one separator and one bioreactor can be used in the loop.

The system can include a nutrient supply, a water source, a surfactant supply, a vapor suppressing foam supply (for tank degassing applications) and/or a means for oxidation of trace metals (which may accumulate in the liquid phase during some applications), all as more fully described in the description below.

In an alternative embodiment of my invention, the foregoing description is modified as follows. A liquid (or other fluid) is circulated through the loop, and a bioreactor is positioned in the loop. The bioreactor contains a microorganism effective for the biodegradation of the contaminant. The liquid passes through the bioreactor and the contaminant is introduced into the bioreactor for biodegradation. A bio-agent (having a microorganism) is not necessarily circulated through the loop. The liquid serves as an absorption medium to separate contaminant from the gas phase.

In the preferred embodiments of my invention a loop is employed as contrasted with other conduit arrangements. A loop provides (i) for recirculation of the bio-agent in the first embodiment described above, and (ii) for recirculation of the liquid in the second embodiment described above. In other embodiments of my invention, the conduit can be in a non-loop arrangement (but in such cases the significant advantages of recirculation are lost). More broadly, my invention is a system in which the contaminated gas is introduced into a conduit in which the bio-agent is flowing, or alternatively, a system in which the contaminated gas is introduced into a conduit through which a liquid (or other fluid flows) and which directs the contaminant into a bioreactor.

My invention also includes the method for decontamination of a contaminated gas as summarized above and as more fully described below.

DETAILED DESCRIPTION OF THE INVENTION

Figure 1:
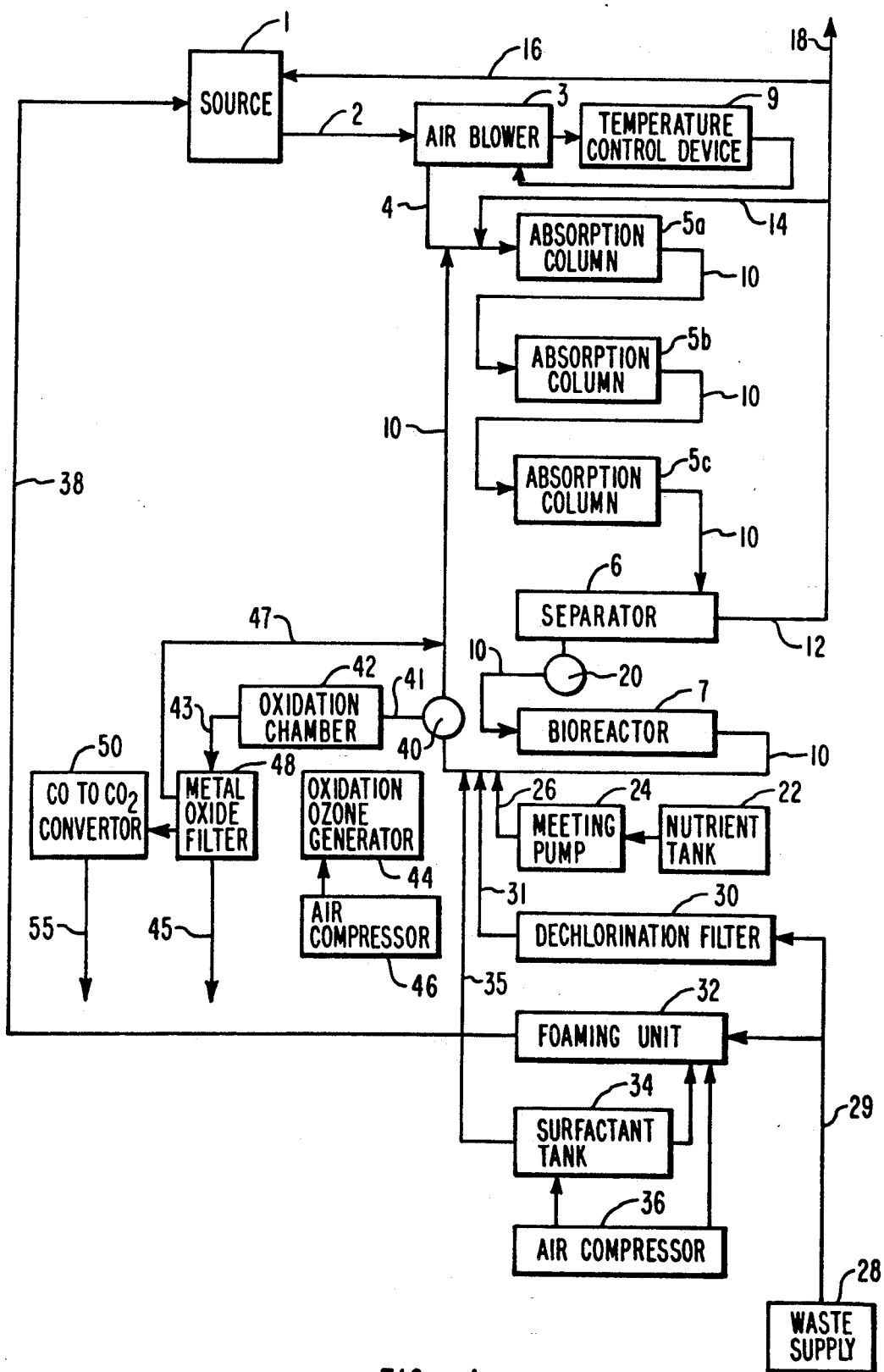
FIG. 1 depicts an embodiment of the decontamination system of this invention.
Figure 2:
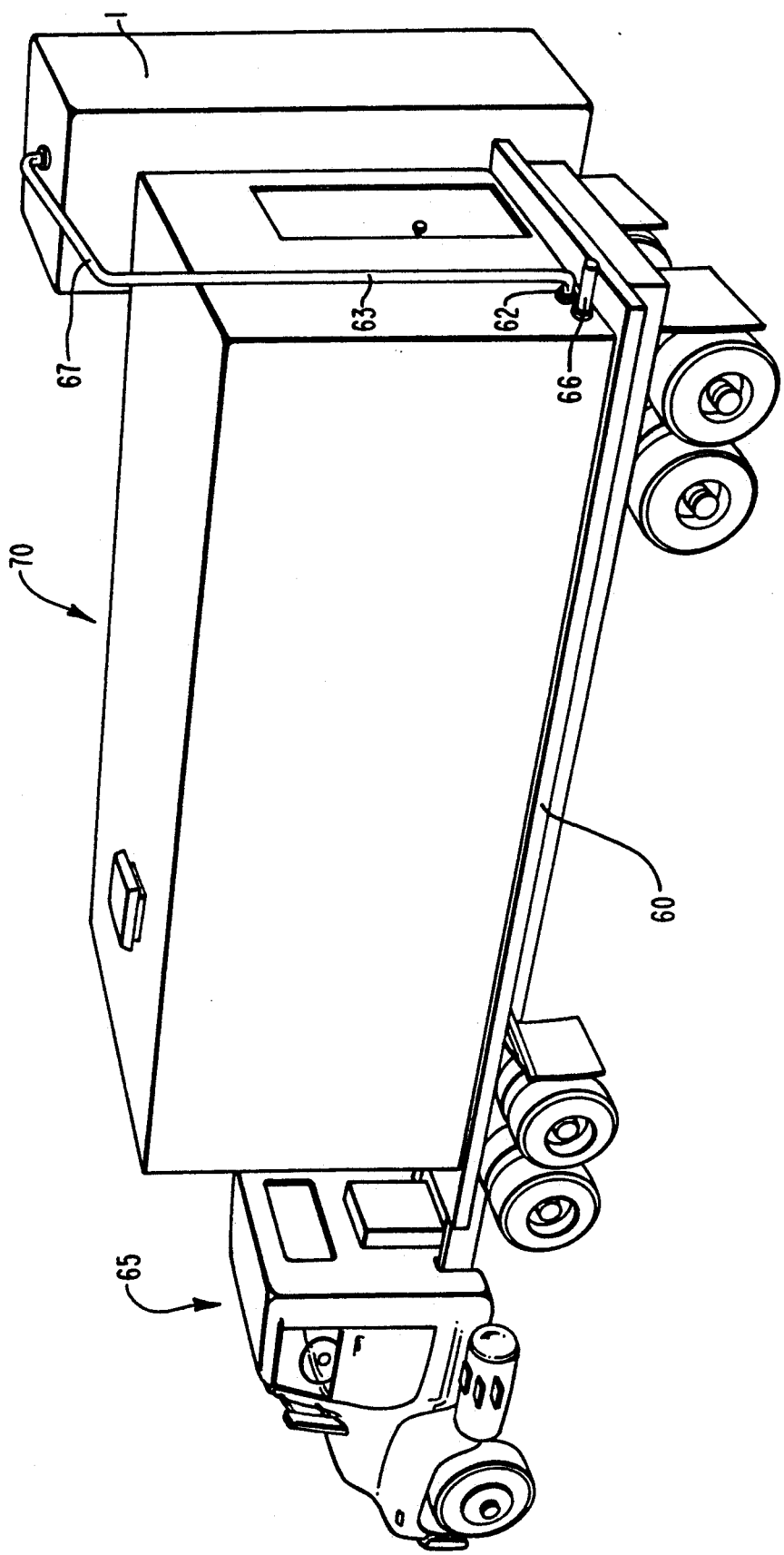
FIG. 2 depicts a trailer supporting a decontamination system.
Figure 1:
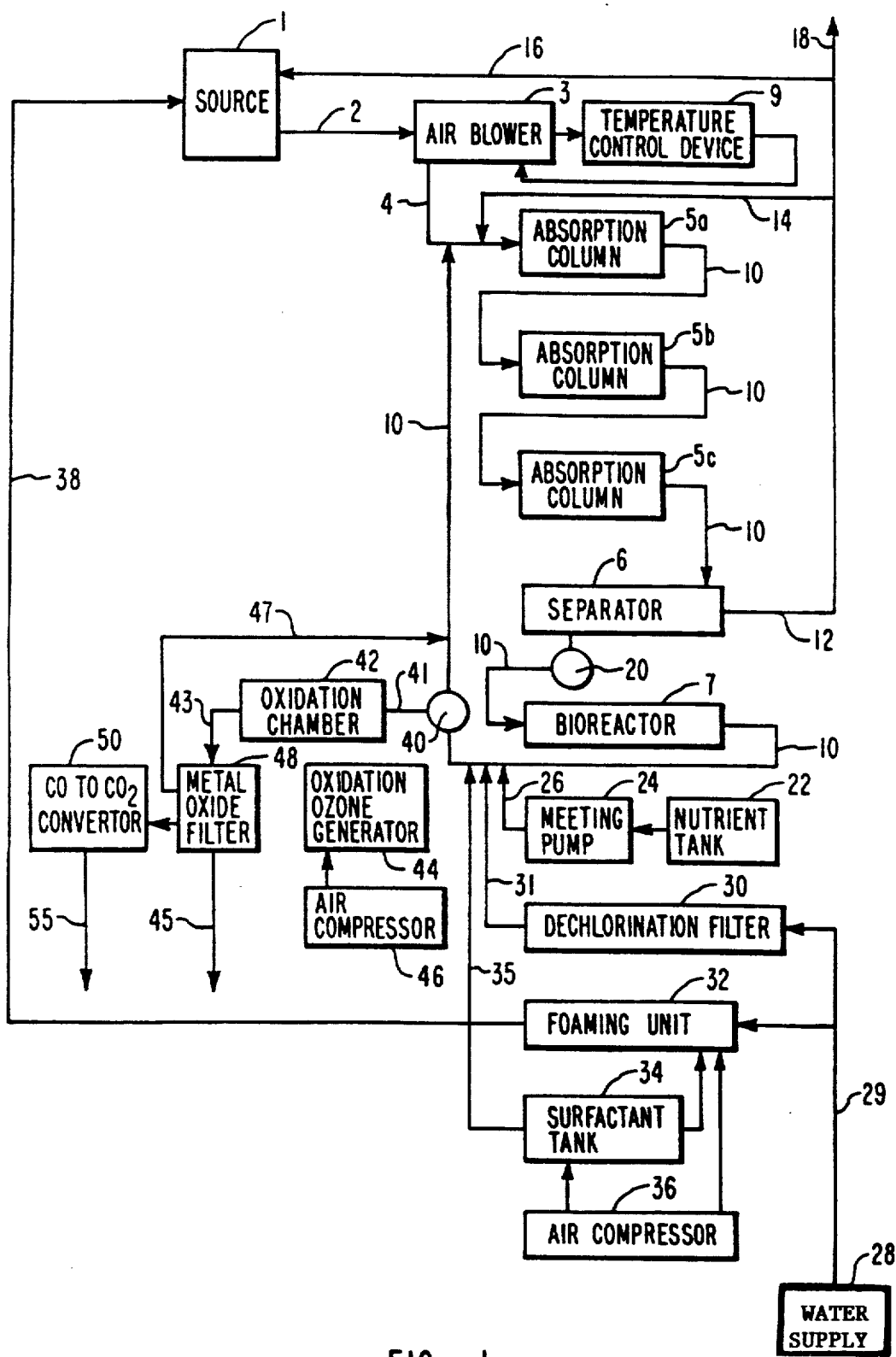

FIG. 1 depicts an embodiment of the inventive decontamination system. The decontamination system can be used to decontaminate contaminated gas from a source 1. Source 1 can be any of the following: (a) an enclosed contaminated atmosphere in a tank or other storage vessel, (b) a contaminated gas stream (e.g., a contaminated air stream) from an industrial process or facility (e.g. steel mill, petroleum refinery, chemical facility, etc.), (c) contaminated vapor extracted from contaminated soil, (d) contaminated gas from a stripping column and (e) any other source of a contaminated gas.

The contaminated gas can contain one or more contaminants which is (are) susceptible to biodegradation as more fully explained below. Organic compounds can be contaminants in the contaminated gas. Examples of organic compound contaminants include benzene, toluene, xylene, acetone, alcohols, methyl ethyl ketone, tetrahydrofuran, creosote, pentachlorophenol, petroleum hydrocarbons, non-chlorinated solvents (and some chlorinated materials), etc. Sulfur oxides (e.g. $SO_2$, $SO_3$, etc.) and nitrogen oxides (e.g. NO, $NO_2$, $N_2O$, $N_2O_3$, $N_2O_4$, $N_3O_4$, etc.) can also be contaminants in the contaminated gas. These examples are merely illustrative and the practice of my invention is not limited to these contaminants. My invention can be used for the treatment of any contaminant in a gas, provided that a microorganism is available (or can be made available) which is effective for the biodegradation of the contaminant.

A loop 10 is also depicted in FIG. 1. Positioned in Loop 10 are a series of three absorption columns 5a, 5b and 5c, a separator 6 and a bioreactor 7. Pipes or other conduits can be used to construct loop 10 and to connect the absorption columns 5a, 5b and 5c, separator 6 and bioreactor 7 into the loop. A bio-agent is circulated through loop 10 (including absorption columns 5a, 5b and 5c, separator 6 and bioreactor 7). The circulation can be continuous or intermittent. The loop can be any means for holding and/or directing a circulating bio-agent.

Air blower 3 removes contaminated gas from source 1 through line 2 and introduces the contaminated gas into loop 10 through line 4. A commercially available explosion proof blower can, for example, be used as the air blower. Such blower introduces the pressurized contaminated gas into loop 10 and into the base of the first absorption column 5a. Pressure of the blower can typically range from 5 to 200 psi (but this invention is not limited thereto). The air blower can be any air blower, pump or other means for removing contaminated gas from its source and for introducing the contaminated ga into loop 10. More generally, the invention can be practiced with any means for introducing contaminated gas into loop 10.

A temperature control device 9 is used in conjunction with air blower 3 to control the temperature of the contaminated gas. This can be accomplished, for example, by evaporation via water mist. The temperature range can typically range from 40° F. to 90° F. (but this invention is not limited thereto). More generally, the temperature control device can be any means for controlling the temperature of the contaminated gas.

The bio-agent which is circulated through loop 10 can be any microorganism (or microorganisms) effective for the biodegradation of the contaminant. If the contaminated gas contains a plurality of contaminants, a microorganism effective for biodegradation of some or all of such contaminants can be used, or different microorganisms which are differently effective for the biodegradation of the different contaminants can be employed as the bio-agent. The selection of effective microorganisms for my invention is a matter which falls within the knowledge and skill of persons of ordinary skill in the art. Such persons have the requisite knowledge and skill to select and acquire microorganisms which will be effective for biodegradation of the contaminants (or at least those contaminants which the practitioner of the invention targets for treatment). Suitable microorganisms can be selected experimentally (e.g. by trial and error) or from available literature. It rests within the discretion of the practitioner of my invention to select the microorganisms which he/she desires to use for the contaminants targeted by him/her.

Preferably, the microorganisms are bacteria. For example, an oxidizing bacterial culture such as Pseudomonas spp. can be used. Pseudomonas spp. is effective for the biodegradation of organic contaminants such as benzene, toluene, xylene, jet fuel, crude oils, carbohydrates, soluble or insoluble carbonaceous particulates, etc. Other bacteria are also effective for biodegradation of organic compounds.

Bacteria such as Aztobacter and Clostridium are effective for the biodegradation of nitrogen oxides. Bacteria such as Ferroxidans and Thioparusare effective for the biodegradation of sulfur compounds. Other bacteria effective for biodegradation of nitrogen oxides or reduction of sulfur oxides can be used in the practice of my invention.

In addition to effective bacteria, other microorganisms, such as enzymatic agents (e.g. lignin peroxidase), algae, etc., which are effective for biodegration of contaminants, can be used in the practice of my invention. The term "microorganism", as used herein, is intended to include any enzyme produced by a microorganism, or any derivative from a microorganism, which is effective for biodegradation of the contaminant or any synthesized or genetically engineered duplication of such enzyme or derivative.

Preferably, the bacteria (or other microorganisms) are acclimated to the contaminants prior to use. Acclimation of bacteria can be achieved by isolating the bacteria (e.g. a generic strain of Pseudomonas spp) and providing the bacteria with nutrients to strengthen the bacteria. Then the targeted contaminant is fed to the bacteria. The bacteria, over time, become acclimated to the contaminant. They are dependent upon the contaminant as their feed (or carbon source). Nutrients may be added to supplement the contaminant feed. As a result of this acclimation, bacteria strains (e.g. strains of Pseudomonas spp) are grown which are especially effective in biodegrading the contaminant. The strains which can digest the contaminant survive and thrive. Other strains die. Acclimation of bacteria is a subject beyond the scope of my invention. The knowledge and skills of persons of ordinary skill in the art are such as to enable such persons to acclimate bacteria or to acquire acclimated bacteria suitable for us in the practice of my invention. To the extent that acclimation of other microorganisms to contaminants is feasible, such acclimated microorganisms can also be used.

The bio-agent preferably includes, in addition to the microorganism, a liquid carrier. The liquid carrier serves as a carrier for the microorganism, i.e., facilitates circulation of the microorganism through loop 10. The liquid carrier should be effective for absorption of the contaminant from the contaminated gas into the liquid carrier. This facilitates biodegradation of the contaminant by the microorganism. Preferably, the liquid carrier is water or a water based solution. The liquid carrier can contain one or more surfactants or other absorption promoting agents. More generally, the liquid carrier can be any liquid which can serve as a carrier for the microorganism and, preferably provide a liquid phase for absorption of the contaminant. As used herein, "absorption" is intended to also include within its meaning, the capture of particulate contaminants (e.g., particulates which result in PM-10 violations under the Clean Air Act).

Bioreactor 7 contains a microorganism effective for biodegradation of the contaminant. A bioreactor can be any vessel (or even loop or conduit segment) in which the microorganism is resident. A vessel adapted to contain the microorganism is preferred. Alternatively, a filter or other blocking means, can be employed to contain the microorganism within a segment of the loop (or conduit). Absorption columns 5a, 5b and 5c can also contain a microorganism effective for biodegradation of the contaminant (in which case the absorption columns also serve as bioreactors). The microorganism in the absorption columns or bioreactor can be of the same kind as the microorganism in the circulating bio-agent or it can be of a different kind. The discussion above concerning microorganisms, the selection of suitable microorganisms, the preferability of bacteria, the acclimation of bacteria, the examples given, etc. all apply to the microorganism in the absorption columns or bioreactor.

Absorption columns 5a, 5b and 5c and bioreactor 7 are preferably packed with packing. The packing serves as a substrate which supports the microorganism (or microorganisms) resident in the columns and bioreactor.

Preferably, the packing is in the form of spherical-shaped "tri-packs" (which are commercially available as packing for columns). The tri-packs (or "bio-balls") are, essentially, stacked disks arranged and sized to approximate the shape and form of a sphere. The tri-packs provide a substantial surface area for supporting the microorganism. In this embodiment of the invention, the tri-packs in absorption columns 5a, 5b and 5c and bioreactor 7 have a one inch diameter and provide approximately 80 square feet of surface area per cubic foot. Other sizes, forms and kinds of packing can be used in the practice of my invention. For example, flat disks, volcanic rock (such as scoria) and other substrates capable of supporting the bacteria (or other microorganisms) can be used. The packing is a means for supporting the microorganism. The greater the surface area of the packing covered by microorganism, the greater the opportunity for contact of contaminant with microorganism for biodegradation.

Absorption columns 5a, 5b and 5c serve as a means for facilitating absorption by the liquid carrier (liquid phase) of the contaminants from the gas (the gas phase). The liquid carrier, e.g. water, absorbs contaminants. More generally, the absorption columns serve as a means for purging contaminants from the gas (the gas phase) by transferring contaminants from the contaminated gas (gas phase) to the bio-agent (liquid phase). As the contaminated gas, in the form of bubbles, rises through each absorption column, the bubbles strike the packing and bubble size is decreased, which, in turn, facilitates absorption of contaminants from the gas and into the liquid carrier (liquid phase).

Because each absorption column contains a microorganism, it can also function as a pre-separation bioreactor (i.e. as bioreactors positioned in loop 10 downstream from the introduction of contaminated gas 4 into loop 10 and upstream to separator 6). The additional quantities of microorganism effective for biodegradation of contaminants and the relatively large surface area for supporting such microorganism facilitate the biodegradation of contaminants.

As the gas (gas phase) in the form of bubbles and the bio-agent (liquid phase) circulate from the top of an absorption column downward through loop 10 to the bottom of the next absorption column, the size of the bubbles decreases with depth, due to increasing pressure. This results in an increase in the concentration per unit volume of the contaminant in the gas. Because of the increased concentration of contaminant in the gas, the resultant concentration differential between the bubble and liquid causes further absorption of contaminant by the liquid carrier. My invention may contain any number of absorption columns.

Purged gas (i.e. gas with a reduced concentration of contaminant or with less contaminant) and bio-agent (with absorbed contaminant in the liquid carrier) exit absorption column 5c and are introduced into separator 6. Separator 6 can be any means for separating the purged gas (i.e. gas phase) from the bio-agent (liquid phase). At this stage in the process, the separated gas contains no contaminant, or more realistically, a reduced concentration of the contaminant or less contaminant. This is achieved by the absorption by the bio-agent (liquid phase) of the contaminant from the gas. The foregoing describes a means for removing the gas phase from loop 10. The removed (i.e separated) gas 12 can be: (i) reintroduced through line 14 into loop 10 for further biodegradation of remaining contaminant, (ii) recycled through line 16 to source 1 where it is available for reintroduction into loop 10 via lines 2 and 4 for further biodegradation of remaining contaminant, or (iii) released through line 18 into the earth's atmosphere if the concentration of remaining contaminant is sufficiently low, or (iv) directed to a second loop for further biodegradation of the same or different contaminant. Both (i) and (ii) are means for reintroducing the removed gas (gas phase) into loop 10. The reintroduction of removed gas either through line 14 or through line 4 (via line 16) is at a position in loop 10 which is upstream of bioreactor 7 (i.e. the reintroduced gas passes to separation 6 which precedes bioreactor 7).

It should be noted that the separated ga phase removed via line 12 will also include the gaseous products of the biodegradation. For example, aerobic bacteria will convert organic contaminants to carbon dioxide and water and, therefore, it is expected that carbon dioxide and water vapor will be included in the removed gas phase.

It should also be noted that the contaminated gas from source 1 can consist entirely of contaminant (or contaminants) in gaseous form, for example, an organic vapor within a gasoline tank. In such case, the gas phase consists of the gaseous contaminant (or contaminants) and separated gas 12 consists of gaseous contaminant (or contaminants) which has (have) not been absorbed by the liquid carrier. Because the gas phase consists entirely of gaseous contaminant (or contaminants) in this case, the purged gas which is removed via 12 does not have a lower concentration of contaminant (it is still 100%) (except to the extent that the gas phase has been diluted with water vapor and/or other gaseous products of biodegadation) but the quantity of contaminant in the gas phase is less (because of absorption of contaminant by the liquid carrier).

More typically, the contaminated gas from source 1 will include noncontaminated gaseous matter. For example, a contaminated air stream includes air as a non-contaminant. In such case, the concentration of contaminant (or contaminants) in the purged gas decreases as contaminant (or contaminants) is (are) absorbed by the liquid phase.

In this embodiment of my invention, separator 6 is a gravity separator. Separator 6 can, optionally, contain packing (e.g. "tri-pack" as in the absorption columns) up to the free fall air space of the separator. In this embodiment, separator 6 is 80% filled and, therefore, has a 20% head space. The separator 6 is filled with packing (and the microorganism, supported by such packing) to facilitate further reaction of contaminant with microorganism for biodegradation of contaminant.

In the practice of my invention, any means for separating a gas/liquid dispersion can be used as the separation means 6. Equipment and processes for such gas/liquid separations are well known to persons of ordinary skill in the art.

Bio-agent and absorbed contaminants are introduced via pump 20 into bioreactor 7. Bioreactor 7 is a post-separation bioreactor. Bioreactor contains a microorganism (or microorganisms) effective for the biodegradation of the contaminant. The microorganism is supported by packing as previously described. Bioreactor 7 also contains circulating bio-agent (including the microorganism of the bio-agent effective for biodegradation of the contaminant). The purpose of bioreactor 7 is to facilitate and provide further opportunity for biodegradation of the contaminant absorbed in the liquid carrier. Because bioreactor 7 is a post-separation bioreactor, the resident microorganism is not subjected to any potentially adverse effects of direct exposure to the gas phase.

Throughout loop 10 biodegradation reactions occur and the products of these biodegradation reactions (including intermediate products) are circulated through loop 10. The end products of the biodegradation by aerobic bacteria of organic contaminants typically include water and carbon dioxide which can be safely released to the environment. The end product of the biodegradation of nitrogen oxides is nitrogen which can be safely released to the earth's atmosphere as a normal component of the atmosphere. The end product of the biodegradation of sulfur oxides is reduced sulfur, which can be captured by filtration and recycled for use. As a result of the biodegradation, the contaminant is either destroyed or rendered non-hazardous.

A nutrient tank 22 serves as a source of nutrients for the bacteria (or other microorganisms). This tank can be a commercially available tank suitable for holding the nutrients. More significantly, the inventive system include a source of nutrients and a means for delivery of such nutrients to loop 10. Metering pump 24 and line 26 deliver a controlled or metered amount of nutrients to loop 10 over time. The metering pump can be a commercially available metering pump. The nutrients support and enhance growth of the bacteria (or other microorganism). In the case of bacteria, suitable nutrients include aqueous nitrogen-containing fertilizers. Nutrients such as "Deep Treat" and "Meta-Boost" are commercially available from International Remediation Corporation. Nutrients can also include a dissolved oxygen buffer (e.g., dissolved hydrogen peroxide in low concentration).

Water is supplied to loop 10 from water supply 28 via lines 29 and 31. Dechlorination filter 30 removes chlorine from the water because of the harmful effect of chlorine on bacteria (or other microorganisms). The dechlorination filter 30 can be, for example, a commercially available activated carbon tank filter effective for the removal of chlorine.

A surfactant (or detergent or dispersent or colloidal suspension which are regarded by me to be equivalent to a surfactant for purposes of this disclosure and the appended claims) can be introduced into loop 10 from surfactant tank 34 via line 35. The surfactant can be, for example, Bio-Solve from Metrachem, Inc. (other surfactants can be used in the practice of this invention) The purpose of the surfactant is to promote the formation of smaller bubbles, thereby increasing surface area and enhancing the efficiency of absorption of the contaminant.

Air compressor 36 serves to drive surfactant foam through line 38 to source 1, if source 1 is a tank. This air compressor can be a commercially available air compressor. Foaming unit 32 serves as a means for producing a vapor suppressing foam. If source 1 is a tank (or other enclosed atmosphere) it may be desirable to suppress the unwanted escape of contaminated vapor from the tank into the earth's atmosphere. Foam from foaming unit 32 is directed via line 38 to the bank (represented by source 1) to lay down a vapor suppressing foam over the interior bottom of the tank. The foam (including surfactant) accumulates on the bottom of the tank to suppress the formation of additional vapor. Foam is preferably applied to the tank before the decontamination system begins operation (i.e. before contaminated gas is removed from the tank and introduced into loop 10 for treatment).

The contaminated gas may contain hazardous metals which are introduced into loop 10 with the contaminated gas. To deal with such metals, the system may, optionally, include a means for oxidation of the metals and for removal of the resultant metal oxides. To accomplish this, time valve 40 may be used to divert the stream (or a portion thereof) in loop 10 from loop 10 to oxidation chamber 42 via line 41. This stream contains the circulating bio-agent, absorbed contaminant, biodegradation reaction products and the metals. The diversion of the stream may be continuous or as a batch. The diversion can be timed by time valve 40.

Oxidation/ozone generator 44 supplies oxidation solutions and/or ozone saturated solutions to oxidation chamber 42. Examples of possible oxidation solutions include, but are not limited to, isopropyl, peroxide, chloride or potassium permanganate. Ozone is supplied when the effectiveness of the oxidation needs to be increased or maximized. Oxidation chamber 42 can be a mixing chamber in which the diverted stream and oxidation solution (and/or ozone saturated solution) are mixed. Ionic metals in the stream are oxidized in chamber 42. The resultant metal oxides and the stream are directed via line 43 to metal oxide filter 48. Filter 48 traps the metal oxides and allows the de-metalized stream to be returned via line 47 to loop 10. Metal oxides can be removed from filter 48 and sent to metal recyclers for reuse (such removal is represented by line 45). Carbon monoxide can be directed via line 49 to converter 50 for conversion of carbon monoxide (CO) into carbon dioxide ($CO_2$). Carbon dioxide is vented into the earth's atmosphere via line 55. Air compressor 46 supplies air to oxidation/ozone generator 44 as depicted in FIG. 1.

In this embodiment of the invention the conduit is in the form of a loop, i.e., the bio-agent is recirculated (and the liquid carrier is recirculated) to provide for multiple passe through the loop. This allows for multiple passes of contaminant through bioreactor 7. If the conduit is not in the form of a loop, the advantages of a loop are lost. For example, contaminated gas can be introduced into the conduit for contact with the bio-agent flowing through the conduit but would only pass through absorption columns 5*a*, 5*b* and 5*c* once (and the contaminant would only pass through bio-reactor 7 once).

Loop 10 is preferably a closed loop (as shown in FIG. 1). A closed loop is a loop which isolates the circulating contaminant from the earth's atmosphere (except to the extent, if any, that contaminant in the removed gas phase intentionally released into the earth's atmosphere—see, e.g., line 18).

Loop 10 should be operated within the temperature parameters suitable for the microorganisms in loop 10 and absorption columns 5*a*, 5*b* and 5*c* and bioreactor 7. If the temperature is too cool, the biodegradation will be inhibited. If the temperature is too high, the microorganism may be killed. Optional operating temperatures will be determined by the practitioners of my invention for the microorganisms which they select for use. Similarly, pH levels, the introduction of dissolved oxygen (for, e.g., aerobic bacteria) and a proper balance of nitrogen and phosphorous nutrients will depend upon the microorganisms selected by the practitioner. Such determinations are matters within the scope of skill and knowledge of persons of ordinary skill in the art.

The decontamination system can be transportable to source 1. This is preferrable for applications such as the degassing of tanks where mobility of the system is desired so that different tanks (or other sources) can be treated. The loop 10 (including absorption columns 5*a*, 5*b* and 5*c*, separator 6 and bioreactor 7) can be supported on transportable support, such as a trailer, and transported to source 1. Optionally, other components, e.g., air blower 3, nutrient tank 22, dechlorination filter 30, foaming unit 32, oxidation chamber 42, etc., can also be supported on the transportable support. This mobility renders the system more cost effective and more versatile in mitigating or remediating contaminated sources. FIG. 2 depicts a trailer 60 which supports the system, as described above, in housing 70. Vehicle 65 can tow trailer 60 and system 70 to various sources for decontamination purposes. Influent port 62 connects to source 1 via conduit 63 for introduction of contaminated gas into the loop. Port 66 is an effluent port.

A brief summary of the inventive process is given below for a contaminated air stream. The example is more generally applicable to a contaminated gas and should be read with this in mind.

A contaminated air stream from source 1 is removed from source 1 by air blower 3 via line 2 and is introduced into loop 10 via line 4. The contaminated air contains air and a contaminant. The contaminated air is introduced into loop 10 for contact with a bio-agent circulating in loop 10. The bio-agent contains bacteria effective for biodegradation of the contaminant and a liquid carrier effective for absorption of the contaminant. With reference from the point of introduction into the loop (i.e. line 4 into loop 10), the absorption columns 5*a*, 5*b* and 5*c* are upstream from the separator 6 and bioreactor 7, and the bioreactor 7 is downstream from separator 6.

The contaminated air is circulated with the bioagent through absorption columns 5*a*, 5*b* and 5*c* to purge the air of the contaminant (i.e. to reduce the concentration of contaminant in the air). Purged air is separated from the liquid phase (bio-agent and absorbed contaminant) in separator 6. Separated purged air is removed from loop 10 via line 12. The liquid phase is circulated through bioreactor 7 for further biodegradation of contaminant by bacteria resident in bioreactor 7. The liquid phase exits bioreactor 7 for return to absorption columns 5*a*, 5*b* and 5*c*.

In another embodiment of my invention, the circulating bio-agent is replaced by a liquid (or other fluid). The liquid can be the same as the liquid carrier described previously. In such embodiment, there is no circulating microorganism for biodegradation of the contaminant. Biodegradation does occur, however, in the bio-reactor(s) through which the liquid circulates. The liquid serves as an absorption medium to absorp the contaminant from the gas phase.

The foregoing description of my invention and the drawings so fully reveal the general nature and the innovations and advantages of my invention that others can readily modify such invention and/or adapt it for various applications without departing from its general concepts, and, therefore such adaptations and modifications should be and are intended to be comprehended within the meaning and range of the claims appended hereto and their equivalents, which claims define subject matter regarded by me to be my invention.

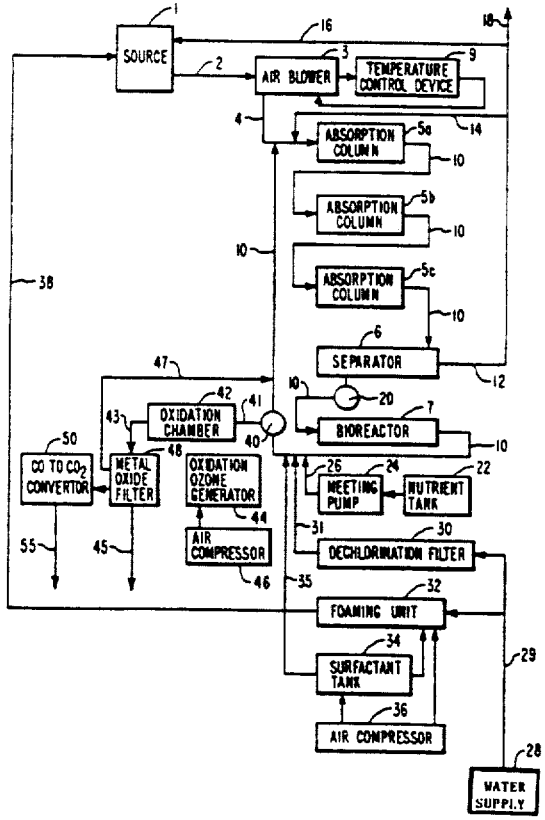

I claim:

1. A decontamination system comprising:
   (a) a source of contaminated gas, said contaminated gas comprising a gas phase and at least one contaminant,
   (b) a loop having a bio-agent therein and said bio-agent is circulated, said bio-agent comprising a microorganism effective for biodegradation of said at least one contaminant, and
   (c) an introduction means for introducing said contaminated gas into said loop for contact of said contaminated gas with said bio-agent and for biodegradation of said at least one contaminant by said microorganism, and for circulation of said contaminated gas in said loop with said bio-agent.

2. A decontamination system in accordance with claim 1 further comprising:
   (d) a separation means for removal of said gas phase from said loop.

3. A decontamination system in accordance with claim 2 wherein said separation means is a gravity separator.

4. A decontamination system in accordance with claim 1 further comprising:
   (d) a bioreactor which is positioned in said loop and through which said bio-agent passes and into which said at least one contaminant is introduced; wherein a microorganism is resident in said bioreactor, said microorganism in said bioreactor being effective for biodegradation of said at least one contaminant.

5. A decontamination system in accordance with claim 4 wherein said bioreactor is a vessel which contains packing supporting the microorganism resident in said bioreactor; wherein said packing is positioned in said vessel to allow contact of the supported microorganism with said at least one contaminant introduced into said bioreactor.

6. A decontamination system in accordance with claim 5 wherein said supported microorganism is of the same kind as the microorganism of said circulating bio-agent.

7. A decontamination system in accordance with claim 5 wherein said supported microorganism is of a different kind than that of the microorganism of said circulating bio-agent.

8. A decontamination system in accordance with claim 1 wherein said bio-agent further comprises a liquid carrier to facilitate circulation of said microorganism in said loop.

9. A decontamination system in accordance with claim 8 wherein said liquid carrier comprises water.

10. A decontamination system in accordance with claim 8 wherein said liquid carrier is effective for absorption of said at least one contaminant from said contaminated gas.

11. A decontamination system in accordance with claim 10 further comprising:
    (d) an absorption column to facilitate said absorption of said at least one contaminant from said contaminated gas.

12. A decontamination system in accordance with claim 11 wherein said absorption column contains packing supporting a microorganism effective for biodegradation of said at least one contaminant.

13. A decontamination system in accordance with claim 1 further comprising:
    (d) a nutrient supply, and
    (e) a means for supplying nutrient from said nutrient supply to said loop;
    wherein said nutrient is a nutrient which enhances growth of said microorganism.

14. A decontamination system in accordance with claim 1 wherein said contaminated gas contains at least one metal; and wherein said decontamination system further comprises an oxidation means for oxidizing said at least one metal to produce at least one metal oxide.

15. A decontamination system in accordance with claim 14 further comprising a means for diverting a stream from said loop to said oxidation means; wherein said stream comprises said bio-agent and said at least one metal.

16. A decontamination system in accordance with claim 15 further comprising a filter effective for filtration of said at least one metal oxide.

17. A decontamination system in accordance with claim 15 wherein said contaminanted gas includes a second contaminant in the form of CO; and wherein said decontamination system further comprises a convertor for conversion of said CO to $CO_2$.

18. A decontamination system in accordance with claim 1 further comprising:
    (d) a water supply, and
    (e) a means for supplying water from said water supply to said loop.

19. A decontamination system in accordance with claim 1 further comprising:
    (d) a surfactant supply, and
    (e) a means for supplying surfactant from said surfactant supply to said loop.

20. A decontamination system in accordance with claim 1 further comprising:
    (d) a separation means for removal of said gas phase from said loop, and
    (e) a means for reintroducing said removed gas phase to said loop.

21. A decontamination system in accordance with claim 1 further comprising:
    (d) a separation means for removal of said gas phase from said loop, and
    (e) a post-separation bioreactor which is positioned in said loop and through which said bio-agent passes and into which said at least one contaminant is introduced;
    wherein said bioreactor contains a microorganism effective for the biodegradation of said at least one contaminant; and wherein said bio-agent further comprises a liquid carrier which is effective for absorption of said at least one contaminant from said contaminated gas.

22. A decontamination system in accordance with claim 21 further comprising:
(f) an absorption column positioned in said loop upstream to said separation means and through which said bio-agent and said contaminated gas pass;
wherein said absorption column is a means for facilitating absorption of said at least one contaminant by said liquid carrier.

23. A decontamination system in accordance with claim 22 further comprising:
(g) a means for returning and reintroducing said removed gas phase to said loop;
wherein said removed gas phase is returned to a position in said loop which precedes said absorption column and, therefore, allows for reintroduction of said removed gas phase into said absorption column; and wherein said position is upstream from said bioreactor so that said removed gas phase is not passed through said bioreactor.

24. A decontamination system in accordance with claim 22 wherein said absorption column contains packing supporting a microorganism effective for biodegradation of said at least one contaminant; and wherein said post-separation bioreactor is a vessel containing packing which supports the microorganism contained in said bioreactor.

25. A decontamination system in accordance with claim 22 further comprising:
(g) a nutrient supply, and
(h) a means for supplying nutrient from said nutrient supply to said loop;
wherein said nutrient is a nutrient which enhances growth of said microorganisms.

26. A decontamination system in accordance with claim 25 further comprising:
(i) a water supply, and
(j) a means for supplying water from said water supply to said loop.

27. A decontamination system in accordance with claim 26 further comprising:
(k) a surfactant supply, and
(l) a means for supplying surfactant from said surfactant supply to said loop.

28. A decontamination system in accordance with claim 22 wherein said contaminated gas further comprises at least one metal; and wherein said decontamination system further comprises
an oxidation chamber for oxidizing said at least one metal.

29. A decontamination system in accordance with claim 1 wherein said source is a contaminated soil, and said contamination gas is a contaminated soil vapor.

30. A decontamination system in accordance with claim 1 wherein said microorganism is a bacterium.

31. A decontamination system in accordance with claim 22 wherein the microorganisms are bacteria.

32. A decontamination system in accordance with claim 1 wherein said source of contaminated gas is a tank; wherein said contaminated gas is a contaminated vapor; and wherein said system further comprises a means for supplying foam and a means for applying said foam to said tank to suppress escape of contaminated vapor from said tank.

33. A decontamination system in accordance with claim 1 wherein said loop is a closed loop.

34. A decontamination system in accordance with claim 2 wherein said loop is a closed loop.

35. A decontamination system for decontamination of a contaminated gas comprising a gas phase and a contaminant, said system comprising a loop having a bis-agent therein and through which said bio-agent is circulated and into which said contaminated gas can be introduced; wherein said bio-agent comprises (i) a microorganism effective for biodegradation of said contaminant, and (ii) a liquid carrier effective for absorption of said contaminant from said gas phase; and wherein introduction of said contaminated gas into said loop allows for contact of said contaminated gas with said bio-agent and for absorption of said contaminant by said liquid carrier, and for biodegradation of said contaminant by said microorganism, and for circulation of said contaminated gas in said loop with said bio-agent.

36. A decontamination system in accordance with claim 35 further comprising a separation means for separating said gas phase from said loop and said circulating bio-agent.

37. A decontamination system in accordance with claim 36 further comprising a bioreactor which is positioned in said loop and through which said bio-agent passes and into which said contaminant is introduced; wherein said bioreactor contains a microorganism effective for biodegradation of said contaminant; and wherein said bioreactor is positioned downstream of said separation means to receive said circulating bio-agent and said contaminant absorbed in said liquid carrier after they exit said separation means.

38. A decontamination system in accordance with claim 37 further comprising an absorption column positioned in said loop to facilitate said absorption of said contaminant and through which said bio-agent and said contaminated gas pass.

39. A decontamination system in accordance with claim 38 wherein said absorption column, said separation means and said bioreactor are positioned such that said contaminated gas, after introduction into said loop, is first circulated to said absorption column.

40. A decontamination system in accordance with claim 39 further comprising a means for supplying nutrient to said loop; wherein said nutrient is a nutrient which enhances growth of said microorganisms.

41. A decontamination system in accordance with claim 40 further comprising a means for supplying water to said loop.

42. A decontamination system in accordance with claim 37 wherein said contaminated gas further comprises a metal; and wherein said decontamination system further comprises:
(a) an oxidation means for oxidizing said metal to produce a metal oxide, and
(b) a means for diverting a stream from said loop to said oxidation means;
wherein said stream comprises said bio-agent and said metal.

43. A decontamination system in accordance with claim 35 wherein said microorganism is a bacterium.

44. A decontamination system in accordance with claim 37 wherein said microorganisms are bacteria.

45. A decontamination system in accordance with claim 44 wherein said contaminant is an organic compound, and wherein said bacteria are Pseudomonas spp.

46. A decontamination system in accordance with claim 44 wherein said contaminant is a sulfur oxide.

47. A decontamination system in accordance with claim 44 wherein said contaminant is a nitrogen oxide.

48. A decontamination system in accordance with claim 35 wherein said contaminated gas is contaminated air.

49. A decontamination system in accordance with claim 35 wherein said loop is supported on a transportable support.

50. A decontamination system in accordance with claim 42 wherein said system is supported on a transportable support.

51. A decontamination system in accordance with claim 35 wherein said loop is a closed loop.

52. A decontamination system in accordance with claim 38 wherein said loop is a closed loop.

53. A decontamination system in accordance with claim 36 further comprising at least one pre-separation bioreactor containing a microorganism effective for the biodegradation of said contaminant and at least one post-separation bioreactor containing a microorganism effective for the biodegradation of said contaminant.

54. A method for decontaminating a contaminated gas comprising a gas phase and a contaminant, said method comprising:
    (a) circulating a bio-agent in a loop, said bio-agent comprising a microorganism effective for biodegradation of said contaminant,
    (b) introducing said contaminated gas into said loop for contact of said contaminated gas with said bio-agent and for circulation of said contaminated gas in said loop with said bio-agent, and
    (c) biodegrading said contaminant by said microorganism in said loop.

55. A method in accordance with claim 54 further comprising:
    (d) purging said contaminated gas of said contaminant, and
    (e) separating said purged gas from said loop.

56. A method for decontaminating a contaminated gas comprising a gas phase and a contaminant, said method comprising:
    (a) circulating a bio-agent in a loop, said bio-agent comprising (i) a microorganism effective for biodegradation of said contaminant and (ii) a liquid carrier effective for absorption of said contaminant,
    (b) introducing said contaminated gas into said loop for contact of said contaminated gas with said bio-agent, and for circulation of said contaminated gas in said loop with said bio-agent.
    (c) absorbing said contaminant by said liquid carrier from said contaminated gas,
    (d) biodegrading said contaminant by said microorganism in said loop, and
    (e) separation of said gas phase from said liquid carrier and removal of said separated gas phase from said loop.

57. A method in accordance with claim 56 further comprising:
    (f) reintroducing said removed gas phase into said loop.

58. A method in accordance with claim 56 wherein said contaminated gas contains at least one metal; and wherein said method further comprises:
    (f) oxidizing said at least one metal.

59. A method for decontamination of a contaminated gas comprising a gas phase and a contaminant, said method comprising:
    (a) circulating a liquid in a loop, and
    (b) introducing said contaminated gas into said loop for circulation of said contaminated gas in said loop with said liquid;
wherein a bioreactor is positioned in said loop; wherein said liquid is circulated through said bioreactor; wherein a microorganism is resident in said bioreactor; wherein said microorganism is effective for biodegradation of said contaminant; and wherein said contaminant is introduced into said bioreactor for biodegradation by said microorganism.

60. A method in accordance with claim 59 wherein said liquid is effective for absorption of said contaminant from said contaminated gas.

61. A method in accordance with claim 60 further comprising:
    (c) separation said gas phase from said liquid and removal of said separated gas phase from said loop.

62. A method for degassing a tank containing a contaminated gas comprising a gas phase and a contaminant, said method comprising:
    (a) circulating a bio-agent in a loop, said bio-agent comprising a microorganism effective for biodegradation of said contaminant,
    (b) removing said contaminated gas from said tank, and
    (c) introducing said contaminated gas into said loop for contact of said contaminated gas with said bio-agent and for biodegradation of said contaminant by said microorganism and for circulation of said contaminated gas in said loop with said bio-agent.

63. A method in accordance with claim 62 further comprising:
    (d) purging said gas phase of said contaminant, and
    (e) separating said purged gas phase from said loop.

64. A method in accordance with claim 63 wherein said bio-agent further comprises a liquid carrier to facilitate circulation of said microorganism in said loop; and wherein said gas phase is purged by absorption by said liquid carrier of said contaminant from said gas phase.

65. A method in accordance with claim 64 further comprising applying a vapor suppressing foam to said tank.

66. A method for degassing a tank containing a contaminated gas comprising a gas phase and a contaminant, said method comprising:
    (a) circulating a liquid in a loop,
    (b) removing said contaminated gas from said tank, and
    (c) introducing said contaminated gas into said loop for circulation of said contaminated gas in said loop with said liquid;
wherein a bioreactor is positioned in said loop; wherein said liquid is circulated through said bioreactor; wherein a microorganism is resident in said bioreactor; wherein said microorganism is effective for biodegradation of said contaminant; and wherein said contaminant is introduced into said bioreactor for biodegradation by said microorganism.

67. A method in accordance with claim 66 wherein said liquid is effective for absorption of said contaminant from said contaminated gas; and wherein said method further comprises:
    (c) separating of said gas phase from said liquid and removal of said separated gas phase from said loop.

68. A method for decontaminating contaminated soil vapor comprising a vapor phase and a contaminant, said method comprising:
    (a) extracting said contaminated vapor from soil, (b) introducing said extracted contaminated vapor into a loop containing a circulating bio-agent for circulation of said extracted contaminated vapor in said loop with said circulating bio-agent, said bio-agent comprising a microorganism effective for biodegrading said contaminant, and (c) biodegrading said contaminant by said microorganism in said loop.

69. A method in accordance with claim 68 wherein said bio-agent further comprises a liquid carrier effective for absorption of said contaminant from said vapor phase; and wherein said vapor phase is purged by absorption by said liquid carrier of said contaminant from said vapor phase; and wherein purged vapor phase is removed from said loop.

70. A method for decontaminating contaminated soil vapor comprising a vapor phase and a contaminant, said method comprising:

(a) extracting said contaminated vapor from soil, and (b) introducing said extracted contaminated vapor into a loop containing a circulating liquid for circulation of said extracted contaminated vapor in said loop with said circulating liquid, said liquid being effective for absorption of said contaminant from said contaminated vapor;

wherein a bioreactor is positioned in said loop; wherein said liquid is circulated through said bioreactor; wherein a microorganism is resident in said bioreactor; wherein said microorganism is effective for biodegradation of said contaminant; and wherein said contaminant is introduced into said bioreactor for biodegradation by said microorganism.

71. A method in accordance with claim 70 wherein said vapor phase is purged by absorption by said liquid of said contaminant; and wherein purged vapor is removed from said loop.

72. A decontamination system comprising:

(a) a source of contaminated gas, said contaminated gas comprising a gas phase and at least one contaminant, (b) a conduit having a bio-agent therein and through which said bio-agent flows, said bio-agent comprising a microorganism effective for biodegradation of said contaminant, and (c) an introduction means for introducing said contaminated gas into said conduit for contact of said contaminated gas with said bio-agent and for biodegradation of said contaminant by said microorganism, and for circulation of said contaminated gas in said conduit with said bio-agent.

73. A decontamination system in accordance with claim 72 wherein said bio-agent further comprises a liquid carrier.

74. A decontamination system in accordance with claim 73 wherein said liquid carrier is effective for absorption of said contaminant from said contaminated gas.

75. A decontamination system in accordance with claim 74 further comprising:

(d) a separation means for removal of said gas phase from said conduit.

76. A decontamination system in accordance with claim 75 wherein said microorganism is a bacterium.

77. A decontamination system comprising:

(a) a source of contaminated gas, said contaminated gas comprising a gas phase and at least one contaminant, (b) a conduit through which a fluid flows, (c) a bioreactor positioned in said conduit, (d) a microorganism resident in said bioreactor, said microorganism being effective for biodegradation of said at least one contaminant, and (e) an introduction means for introducing said contaminated gas into said conduit;

wherein said conduit directs said at least one contaminant into said bioreactor for contact of said at least one contaminant with said microorganism and for biodegradation of said at least one contaminant by said microorganism.

78. A decontamination system in accordance with claim 77 wherein said fluid is a liquid effective for absorption of said at least one contaminant from said contaminated gas.

79. A decontamination system in accordance with claim 78 further comprising:

(f) a separation means for removal of said gas phase from said conduit;

wherein said bioreactor is a pre-separation bioreactor.

80. A decontamination system in accordance with claim 79 further comprising:

(g) a post-separation bioreactor which is positioned in said conduit and through which said liquid flows;

wherein a microorganism is resident in said post-separation bioreactor; and wherein the bio-agent of said post-separation bioreactor comprises a microorganism effective for biodegradation of at least one contaminant of said contaminated gas.

81. A decontamination system in accordance with claim 80 wherein a bio-agent flows through said conduit; and wherein the bio-agent flowing through said conduit comprises a microorganism effective for biodegradation of at least one contaminant of said contaminated gas.

82. A decontamination system in accordance with claim 77 wherein a bio-agent flows through said conduit; and wherein the bio-agent flowing through said conduit comprises a microorganism effective of biodegradation for at least one contaminant of said contaminated gas.

83. A decontamination system comprising:

(a) a source of contaminated gas, said contaminated gas comprising a gas phase and at least one contaminant, (b) a loop having a liquid therein and through which said liquid is circulated, said liquid being effective for absorption of said at least one contaminant from said contaminated gas, (c) a bioreactor which is positioned in said loop and through which said liquid is circulated and into which said at least one contaminant is introduced, (d) a microorganism resident in said bioreactor, said microorganism being effective for biodegradation of said at least one contaminant, and (e) an introduction means for introducing said contaminated gas into said loop for circulation of said contaminated gas in said loop with said liquid.

84. A decontamination system in accordance with claim 83 further comprising:

(f) a separation means for removal of said gas phase from said loop.

85. A decontamination system in accordance with claim 84 wherein said bioreactor is a post-separation bioreactor and wherein contaminant absorbed by said liquid is biodegraded by said microorganism in said post-separation bioreactor.

86. A decontamination, system in accordance with claim 84 further comprising:
(g) an absorption column to facilitate said absorption of said at least one contaminant from said contaminated gas.

87. A decontamination system in accordance with claim 86 wherein said absorption column contains a microorganism effective for biodegradation of said at least one contaminant.

88. A decontamination system in accordance with claim 84 further comprising:
(g) a nutrient supply, and
(h) a means for supplying nutrient from said nutrient supply to said loop;
wherein said nutrient is a nutrient which enhances growth of said microorganism.

89. A decontamination system in accordance with claim 84 wherein said contaminated gas contains at least one metal; and wherein said decontamination system further comprises an oxidation means for oxidizing said at least one metal to produce at least one metal oxide.

90. A decontamination system in accordance with claim 84 further comprising:
(g) a water supply, and
(h) a means for supplying water from said water supply to said loop.

91. A decontamination system in accordance with claim 84 further comprising:
(g) a surfactant supply, and
(h) a means for supplying surfactant from said surfactant supply to said loop.

92. A decontamination system in accordance with claim 84 further comprising:
(g) a means for reintroducing said removed gas phase to said loop.

93. A decontamination system in accordance with claim 85 further comprising:
(g) an absorption column positioned in said loop upstream to said separation means and through which said liquid and said contaminated gas pass;
wherein said absorption column is a means for facilitating absorption of said at least one contaminant by said liquid.

94. A decontamination system in accordance with claim 93 further comprising:
(h) a means for returning and reintroducing said removed gas phase to said loop;
wherein said removed gas phase is returned to a position in said loop which precedes said absorption column and, therefore, allows for reintroduction of said removed gas phase into said absorption column; and wherein said position is upstream from said bioreactor so that said removed gas phase is not passed through said bioreactor.

95. A decontamination system in accordance with claim 83 wherein said microorganism is a bacterium.

96. A decontamination system in accordance with claim 83 wherein said source of contaminated gas is a tank; wherein said contaminated gas is a contaminated vapor; and wherein said system further comprises means for supplying foam and a means for applying said foam to said tank to suppress escape of contaminated vapor from said tank.

97. A decontamination system in accordance with claim 83 wherein said loop is a closed loop.

98. A transportable decontamination system for decontamination of a contaminated gas comprising a gas phase and a contaminant, said system comprising:
(a) a source of contaminated gas, said contaminated gas comprising a gas phase and a contaminant;
(b) a loop having a liquid therein and through which said liquid can be circulated and into which the contaminated gas can be introduced for circulation of said contaminated gas in said loop with said liquid,
(c) a bioreactor which is positioned in said loop and through which said liquid can be passed and into which the contaminant can be introduced,
(d) a separation means for removal of the gas phase from said loop, and
(e) a transportable support on which (b), (c) and (d) are supported;
wherein said bioreactor contains a microorganism effective for biodegradation of the contaminant introduced into said bioreactor.

* * * * *

UNITED STATES PATENT AND TRADEMARK OFFICE
CERTIFICATE OF CORRECTION

PATENT NO.    : 5,279,963
DATED         : January 18, 1994
INVENTOR(S)   : Michael M. Hobby It is certified that error appears in the above-indentified patent and that said Letters Patent is hereby corrected as shown below:

The title page and Fig. 1 of the drawings should be deleted to appear as per attached.

Signed and Sealed this

Fifth Day of July, 1994

Attest:

BRUCE LEHMAN

Attesting Officer

Commissioner of Patents and Trademarks

United States Patent [19]
Hobby

[11] Patent Number: 5,279,963
[45] Date of Patent: Jan. 18, 1994

[54] SYSTEM FOR THE DECONTAMINATION OF A CONTAMINATED GAS

[76] Inventor: Michael M. Hobby, 2700 Sunset Rd., Ste. D31, Las Vegas, Nev. 89120

[21] Appl. No.: 687,395

[22] Filed: Apr. 18, 1991

[51] Int. Cl.5 .............................................. A61L 9/01
[52] U.S. Cl. ...................... 435/266; 5/228; 210/631; 435/31; 435/299; 435/311; 435/313; 435/315; 95/187; 95/234
[58] Field of Search .................... 55/89, 90, 228; 435/266, 31, 299, 311, 313, 315; 210/601, 605, 611, 617, 622, 625, 631, 195.1, 199, 202, 721, 760, 912

[56] References Cited

U.S. PATENT DOCUMENTS

| | | | |
|---|---|---|---|
| 3,719,028 | 3/1973 | Brooks | 55/85 |
| 4,427,548 | 1/1984 | Quick, Jr. | 210/617 |
| 4,472,181 | 9/1984 | Herrlander | 55/228 |
| 4,710,301 | 12/1987 | Geuens | 210/605 |
| 4,738,695 | 4/1988 | Carr et al. | 55/84 |
| 4,781,732 | 11/1988 | Wondrasch et al. | 55/10 |
| 4,849,114 | 7/1989 | Zeff et al. | 210/747 |
| 4,940,546 | 7/1990 | Vogelpohl et al. | 210/613 |
| 4,970,000 | 11/1990 | Eppler et al. | 210/605 |
| 4,999,302 | 3/1991 | Kahler et al. | 435/266 |
| 5,017,351 | 5/1991 | Rafson | 423/245.2 |
| 5,039,416 | 8/1991 | Loew et al. | 210/631 |
| 5,077,025 | 12/1991 | Glass | 423/245.1 |
| 5,077,208 | 12/1991 | Sublette | 435/168 |

FOREIGN PATENT DOCUMENTS 3601490 7/1987 Fed. Rep. of Germany.

Primary Examiner—Robert J. Warden
Assistant Examiner—Krisanne M. Thornton
Attorney, Agent, or Firm—Jon C. Christiansen

[57] ABSTRACT

A decontamination system and method for the decontamination of a contaminated gas. The contaminated gas is characterized by a gas phase and at least one contaminant. The contaminated gas is removed from its source and is introduced into a loop through which a bio-agent is circulated. The bio-agent includes a microorganism (e.g. bacterium) effective for the biodegradation of the contaminant. The bio-agent may also include a liquid carrier. The loop may include absorption column, separator and bioreactor positioned in the loop. An oxidation means can be utilized to oxidize metals in the contaminated gas. Alternatively, the bio-agent can be replaced by a liquid which circulates through the bioreactor and which is effective for absorption of the contaminant. In other embodiments, the loop can be replaced by a conduit in a form or arrangement other than a loop.

98 Claims, 2 Drawing Sheets